(12) United States Patent
Cohen (10) Patent No.: US 9,795,295 B2
(45) Date of Patent: Oct. 24, 2017

(54) TONOMETER FOR CHECKING THE INTRA-OCULAR PRESSURE THROUGH THE EYELID AND METHOD USING SAME

(71) Applicant: Michael L. Cohen, Tarpon Springs, FL (US)

(72) Inventor: Michael L. Cohen, Tarpon Springs, FL (US)

(73) Assignee: Michael L. Cohen, Tarpon Springs, FL (US)

( * ) Notice: Subject to any disclaimer, the term of this patent is extended or adjusted under 35 U.S.C. 154(b) by 0 days.

(21) Appl. No.: 14/319,531

(22) Filed: Jun. 30, 2014

(65) Prior Publication Data

US 2015/0094560 A1     Apr. 2, 2015

Related U.S. Application Data

(60) Provisional application No. 61/884,659, filed on Sep. 30, 2013.

(51) Int. Cl.
*A61B 3/16*     (2006.01)

(52) U.S. Cl.
CPC .................................... *A61B 3/16* (2013.01)

(58) Field of Classification Search
CPC ...................................................... A61B 3/165
USPC ............ 600/587, 398, 405, 452, 453; 606/4
See application file for complete search history.

(56) References Cited

U.S. PATENT DOCUMENTS

| 2,882,891 | A | | 4/1959 | Husted | |
|---|---|---|---|---|---|
| 2,905,147 | A | | 9/1959 | Johmann | |
| 3,343,293 | A | * | 9/1967 | Kirklen | 40/334 |
| 3,449,946 | A | * | 6/1969 | Mohrman et al. | 600/405 |
| 4,729,378 | A | | 3/1988 | Trittenbass | |
| 4,930,512 | A | * | 6/1990 | Henriksen et al. | 600/452 |
| 5,174,292 | A | * | 12/1992 | Kursar | 600/405 |
| 5,836,873 | A | * | 11/1998 | Fresco | 600/398 |
| 6,394,954 | B1 | | 5/2002 | Piletsky et al. | |
| 7,992,486 | B2 | * | 8/2011 | Constantine | A47J 31/44 99/275 |
| 2002/0049428 | A1 | * | 4/2002 | Bruce | 606/4 |
| 2004/0267108 | A1 | * | 12/2004 | Moore | 600/398 |
| 2009/0260636 | A1 | | 10/2009 | Markstroem | |
| 2011/0054291 | A1 | * | 3/2011 | Enikov et al. | 600/405 |

(Continued)

FOREIGN PATENT DOCUMENTS

GB     5356     0/1912

OTHER PUBLICATIONS

Qasim K. Farhood "Comparative evaluation of intraocular pressure with an air-puff tonometer versus a Goldmann applanation tonometer" Clin Ophtalmol. 2013; 7 Published online Dec. 27, 2012 pp. 23-27.

(Continued)

*Primary Examiner* — Max Hindenburg
*Assistant Examiner* — Jonathan M Foreman
(74) *Attorney, Agent, or Firm* — Smith, Gambrell & Russell, LLP (57) ABSTRACT

A mechanical IOP (intra ocular pressure) monitor includes a cylinder fitted with an ocular plate attached to the cylinder interior. The cylinder interior comprises a mechanism for transducing pressure, detecting intraocular pressure and a signaling component for indicating when a set intraocular pressure is exceeded.

14 Claims, 6 Drawing Sheets

(56) References Cited

U.S. PATENT DOCUMENTS

2011/0160561 A1* 6/2011 Hastings et al. ............. 600/398

OTHER PUBLICATIONS

Diaton "Pen-like non-contact tonometer for IOP measuring" dated Jan. 12, 2015 pp. 1-2.
Shousha, et al. "Comparison of different intraocular pressure measurement techniques in normal eyes, post surface and post lamellar refractive surgery" [Clin Opthamol 2013; 7: pp. 71-79];Dec. 2012.
Liang, et al. "Self-tonometry in Glaucoma Management-Past, Present and Future" [Surv Opthalmol 54 (4) dated Jul.-Aug. 2009] pp. 450-462.
Karani, et al. "Home Intraocular Pressure Measurement Device" dated Feb. 10, 2006 pp. 1-15.
International Search Report dated Jan. 2, 2015 received in International application No. PCT/US2014/054596.

* cited by examiner

TONOMETER FOR CHECKING THE INTRA-OCULAR PRESSURE THROUGH THE EYELID AND METHOD USING SAME

CROSS REFERENCE TO RELATED APPLICATIONS

This application claims the benefit of U.S. Provisional Application No. 61/884,659, filed Sep. 30, 2013.

FIELD OF THE INVENTION

The present application relates to medical arts and particularly to the practice of ophthalmology. The apparatus and related methods may be used for measuring intraocular pressure (IOP) through the eyelid both in the corneal region, and in the sclerotic region of an eye. Advantageously the apparatus and methods are suitable for use without on-site supervision by highly-skilled medical personnel. The apparatus and methods may be used as a screening tool for a large population, but also by an individual who may benefit from collecting data from multiple measurements of intraocular pressure over a period of time.

BACKGROUND OF THE INVENTION

The intraocular pressure (IOP) of a person's eye has been recognized as an important factor in the early detection of ocular disease. Glaucoma, one such disease occurs quite frequently and can be detected by measuring an increase in intraocular pressure. Using accurate and routine screening, glaucoma may be diagnosed and treated before vision is severely compromised. An increase in intraocular pressure is not sensed by the individual but can be measured in the clinic. Treatment can be started before the onset of gradual, but significant vision loss. Vision loss and blindness can be prevented by early detection. Unfortunately, however, at least one-half the population diagnosed with open-angle glaucoma is asymptomatic. Routine screenings are accordingly instrumental in early diagnosis. The measurement of intraocular pressure is formally known as tonometry—A standard eye test that is done to determine fluid pressure inside the eye.

Tonometry has been practiced for over a half century, but even with this history limitations of IOP monitoring, especially diurnal changes, with presently available tools and methods is recognized:

In normal individuals, IOP varies by 2-6 mmHg over the course of a 24-hour period as aqueous humor production changes. Higher IOP is associated with greater fluctuation and a diurnal fluctuation >10 mmHg is suggestive of glaucoma. Many people reach their peak IOP in the morning hours, but others do so in the afternoon, in the evening, or during sleep; still others follow no reproducible pattern. Comparative evaluation of intraocular pressure with an air-puff tonometer versus a Goldmann applanation tonometer Clin Ophthalmol. 2013; 7: 23-27. Published online 2012 Dec. 27.

Unfortunately, the screening instruments presently available to the medical practitioner are unduly complex. Frequent monitoring, preferably by a patient several times a day, is not available. Often these instruments require frequent recalibration and/or require large and expensive analytical apparatus. They are not suitable for routine measurement that would be required for practical self-use.

In the early history intraocular pressure was determined by two common techniques: indentation or applanation tonometry. In indentation technique, a foot plate with a weight-loaded piston, whose specific weight can be varied, is lowered until it indents the cornea and the foot plate comes to rest on the cornea. The piston is forced upward by the resistance of the cornea being indented. As the piston is forced upward, displacement wias transduced through a lever which actuates a pointer. The pointer then reads out the resistance pressure, or distensibility of the eyeball, providing a value for the intraocular pressure. A representative instrument of this type is the Schiotz tonometer.

The disadvantages of an indentation type instrument are the many sources of error inherent in the instrument itself; i.e., it is affected by temperature, fulcrum friction, accumulation of debris on moving parts causing increased friction. The instrument must be frequently recalibrated. In addition, it is clumsy and difficult to use and inadvertent corneal abrasion may subsequently occur. Indentation produces relatively large volume displacement in the eye, which enhances the effects of varying scleral rigidity. All of these recognized sources of error tend to produce erroneous readings.

Current techniques include Goldmann applanation tonometry, air puff tonometry, ocular response analyzer corneal compensated IOP (ORA IOPcc) and Pentacam corrected IOP. See Shousha et al [Clin Opthamol 2013; 7: 71-79] 2013 for a comparison of these methods. Other methods make use of apparatus such as the Ocuton® S, contact lenses fitted with a strain gauge, the "Home-tonometer" by Zeimer, and Wilensky (analyzing reflected light from a probe-corneal interface), the spring compression Proview® Eye Pressure Monitor (Bausch and Lomb), and Tonopen®. Liang et al (2009 [Sury Ophthalmol 54 (4) July-August 2009]. However, none of these incorporate the desired traits of easy use, low cost and accuracy.

In applanation tonometry, the corneal curvature is flattened or applaned by a flat piston. The piston may be of known weight and the area of applanation determined by an indirect method or it may be of known surface area and the intraocular pressure necessary to applane that area is determined by calculating the force necessary to applane that area. Apparatus using pistons of known surface area are (1) Mackay-Marg which uses electronic means for readout, (2) the Goldmann slit lamp which uses an optical means for readout, and (3) the Tonour which uses a pumped pressure readout.

A Goldmann tonometer uses a small probe attached to a microscope to gently flatten part of one's cornea after numbing drops are used. The apparatus uses a double prism mounted on a standard slit lamp. Using a Goldmann type apparatus, the force required to flatten, or applanate, a constant area of the cornea is measured and related to the IOP using the Imbert-Fick principle. Although or perhaps because of a Goldmann device's complexity, Goldmann is considered by many as the standard for any apparatus to be measured against. However, as advised by Goldmann tonometer marketers: "Applanation tonometry may only be performed by healthcare professionals who are qualified by their respective authorities to do so." Haag-Streit International.

Another method that is currently popular is dubbed "the air puff method". Air-puff tonometry is an applanation method where a standardized puff of air flattens a portion of the cornea. The air puff method has an advantage that it is a non-contact method. When properly administered nothing touches the eye thereby avoiding any risk of corneal abrasion. Also, no topical anesthetic is required.

According to Farhood (2013) [Clin Ophthalmol. 2013; 7: 23-27.]:

"The system consists of a central air plenum flanked either side by a light emitter and a light detector. As the pressure of the air pulse directed to the cornea increases to deform the cornea, the corneal surface behaves like a plane mirror, reflecting light to the detector. Corneal applanation is measured by collecting light reflected from the central cornea. A parallel beam of light is directed onto the central cornea at an angle of 30° and the reflected light is measured by a photo detector at an angle of reflection of 30°. The reflected beam of light will be strongest at this angle when the cornea is flat and acting as a plane mirror, rather than as a curved mirror. The instrument records the force of air required to flatten the cornea and displays the IOP that corresponds to that force. The AP tonometer must be used at a set distance from the cornea, and the instrument incorporates an optical alignment system to facilitate this."

A suitable for home use method has been tested and used. As reported by Liang et al (2009 [Sury Ophthalmol 54 (4) July-August 2009]:

"The Proview Eye Pressure Monitor (Bausch & Lomb, Rochester, N.Y.) was invented by Fresco in 1997. It is a spring compression apparatus with a 3.06-mm diameter circular tip that is applied to the superonasal orbit over the upper eyelid while the eye is directed inferotemporally. As increasing pressure is applied to the eye, a visual sensation that has been variously described as like a solar eclipse or a dark circle surrounded by a bright halo is produced, and the measured IOP is read off the scale. The visual sensation is an entopic phenomenon that occurs with deformation of the eyeball and had been described by various authors since Alcmaeon of Croton circa 600 BCE."

One problem inherent in this method, however, is the overestimation of low intraocular pressures and the underestimation of high intraocular pressures. This underestimation would result in false negative results. Posner advocated use of a tonometer with a piston of pre-determined weight which carries a stain on its contact surface. A print of the stain remaining on the piston after contact is transferred to a paper for measurement. The transfer of area of stain remaining on the foot plate, after corneal contact, to a paper strip, which is then measured on a scale, is very difficult to use and produces many erroneous or unreliable readings.

The Goldmann, Mackay-Marg, air puff, and Tonour methods are complicated, expensive and difficult to use and thus, cannot be routinely used in "group screening" instruments.

It is apparent that these and other similar apparatus cannot provide an inexpensive, easily operated, accurate tool for screening the level of intraocular pressure.

Before tonometry, intraocular pressure (IOP) was clinically evaluated using by palpation through a closed upper eyelid. A skilled ophthalmologist can evaluate approximately whether the IOP is normal, increased or decreased. However, this palpation method suffers from subjectivism, leading to uncertainty of quantifiable results. But the proven efficacy of this qualitative method demonstrates that transpalpebral tonometry can be feasible for screening.

An apparatus currently marketed, the Diaton® tonometer, uses transpalpebral tonometry. The commercial acceptance of this further proves accepted efficacy of transpalpebral methods. However, this apparatus includes an expensive electronic apparatus that is not suited for mass distribution and use.

Patient self-monitoring to date has generally been difficult because most commercial devices cannot be patient actuated—a second person is required. In general the expense of the training and equipment requires the devices to be used in a clinical setting Phospenes, the creation of a light sensation without interaction of a photon with retina receptors, have been used for in home testing. External pressure on the eye is known to create a visual sensation. However, the correspondence between IOP and phosphenes is not universally accepted. Additionally, studies of this phenomenon have shown poor reproducibility.

In a 2006 writing, Karani et al recognized a need for in-home, patient operated tonometry. [Priya Karani, Shawn Tan, Lin Xiong, & Cen Zhang, Home Intraocular Pressure Measurement Apparatus]

http://bme227.pratt.duke.edu/downloads/S06/IOP_Proposal.pdf] Here they recognized that because of significant diurnal variation IOP measurement, multiple, but infrequent visits to an ophthalmologist throughout the year were not truly indicative of a patient's IOP. Because of this, they recognized a need for a means for a patient could use to self-monitor IOP. Their goal was to provide a tonometry monitor suitable for individual at-home use with a cost of under $100.

Liang et al (2009 [Sury Ophthalmol 54 (4) July-August 2009] also acknowledged the need for a tonometry measuring instrument and associated method for self-measured tonometry:

We can foresee the self-tonometer becoming an important part of the delivery of care to glaucoma patients. Potentially, it will be able to send readings to a secure central database that automatically flags fluctuating IOPs and alerts the treating ophthalmologist electronically. This will provide great benefit to patients who live remote to their treating ophthalmologist and may be useful for population screening programs.

Partly in response to these recognized needs, the present invention provides an accurate, inexpensive and simple (non-physician, e.g., patient enabled) means for screenings or measurement between clinical office visits. The apparatus is suitably designed so that data can be easily reported electronically to medical professionals who can thereby efficiently monitor a patient's IOP and provide timely modifications to the patient's treatment.

SUMMARY OF THE INVENTION

The present invention provides a solution to a recognized need for an accurate, simple and inexpensive tool and method for monitoring intraocular pressure (IOP). The apparatus is configured to avoid a need for anesthesia and requires no specialized electronic apparatus that could add significant cost or logistic problems. It is designed to be especially useful for self-monitoring of IOP by glaucoma patients since the apparatus is able to track changes, e.g., according to a desired monitoring schedule during a course of treatment or for measuring diurnal variation.

The apparatus is suitable for non-professional use. It is especially configured for use by a person not trained in ophthalmology, perhaps a public health nurse or aide, or simply by the patient. In the example of the drawings, the apparatus is configured as a pen-like apparatus. A cylinder shaped interior houses a spring and ratchet mechanism. A plate surface contacts the eyelid and monitors a force from the interaction of the spring and the intraocular pressure.

The ratchet mechanism coordinates with a display mechanism to indicate whether the pressure is acceptable (PASS)

or is too high (FAIL). Different springs can be used for varying the PASS-FAIL threshold.

The mechanical actions used in this apparatus are proven. The mechanics of this apparatus make use of technology proven and improved by a half century of use. The apparatus builds on the time-tested ratcheting technology used in retractable ball point pens. See, e.g., Johmann U.S. Pat. No. 2,905,147, whose description including drawings of the retracting mechanism is herein incorporated by reference in its entirety.

This home-use tonometer incorporates a clutch-type structure that includes a piston end that when depressed causes a latch actuating element to slide within the barrel and, when pressure is sufficient to move the piston beyond the inner channels, causes a rotation and repositioning of the indicator piston. This operation is like that of a retractable ball pen where, when sufficient force is applied to the retracting button, the point positioning mechanism rotates to a retracted or exposed (writing-ready) position. In this operation, teeth are moved either into engagement with channel lugs or between the lugs so that the driver forces the latch to a position effecting the longitudinal movement of an indicator piston. Depending on the force applied, the longitudinal movement may exceed a threshold that effects engagement of the lugs. When a force (dependent on the IOP) exceeds a desired value, the ratcheting mechanism effects movement causing the ratchet mechanism to click to a new position and indicate the desired pressure was surpassed.

While the apparatus was specifically designed for use for a human, with minor modifications to the housing and/or spring, the apparatus is suitable for animals. For example, dogs and horses are known to be afflicted with glaucoma and are often treated to ameliorate the symptoms.

For a dog PASS/FAIL thresholds similar to humans are generally acceptable. But slight modification may be desired. For horses, many veterinarians accept an IOP range of about 16 mmHg to about 28 mmHg. For horses and some other animals, springs providing higher or lower PASS/FAIL thresholds may be used in the apparatus.

The simplicity and durability of the apparatus enables its manufacture and distribution at an accessible price, and the simplicity of use applies not only to a clinician, but also for use by non-physician public-health workers and especially for at home self-test use.

BRIEF DESCRIPTION OF THE DRAWINGS

The details of the present invention, both as to its structure and operation, can best be understood by referring to the accompanying drawings, in which like reference numbers and designations refer to like elements.

DETAILED DESCRIPTION OF THE INVENTION

According to the invention, the level of intraocular pressure (IOP) is determined by resting the ocular plate 11, a small, preferably, round plate, on the outer surface of the eyelid. Force, provided by the user, compresses an internal spring and rod mechanism. The force also passes through the eyelid to the surface of the eye. Usually the cornea will be beneath the portion of the eyelid contacted by the plate, but the apparatus is capable of obtaining trans-scleral readings as well.

An object of this invention is to provide a apparatus that provides a pass/fail indication of elevated IOPs. Similar to the design of a retractable pen the present invention includes an outer tube, an inner tube, a first sleeve, a second sleeve, an ocular plate, spring actuated ratchet mechanism 7, and pass/fail indicators both sets being audible and visual.

One feature underlying this invention is that by producing springs in selected standardized spring constant and size, the spring compression as probe movement is stopped can be correlated within acceptable tolerances to the Goldmann tonometer. Depending on the tonometer body design, springs are chosen to match (within tolerances) the Goldmann readings for selected pressures.

The resultant spring(s) will be housed within the precisely specified spaces of the front and/or rear sections of the apparatus, will interact with the ratchet mechanism 7 and will yield a pass/fail indication at predetermined pressures and/or pressures selected by the choice of, precise-pressure calibrated spring 5, 15.

Stainless steel springs are in common use. But other wires, such as music wire (high carbon steel) or copper alloys may be used. A wire diameter of about 0.020 to about 0.025" is a preferred size. The pitch (coils/inch) and free-length can also be adjusted as desired to produce a spring with proper calibration. The spring should be mildly compressed to remove play in the system and produce a more solid feel.

Springs, the tube of the device, or any part or portion of the apparatus can be color coded to indicate the calibrated IOP value.

A "Click" sound is made by engaging the ratchet mechanism 7. The ratchet mechanism will become engaged whenever the IOP in the tested eye exceeds the set PASS/FAIL threshold. For example, an IOP of 17 mmHg would indicate FAIL (set pressure exceeded) for devices whose thresholds were set to be 10 mmHg and 14 mmHg (any threshold lower than 17 mmHg) and would still indicate PASS for devices with thresholds set at 18 mmHg and 22 mmHg (any threshold higher than 17 mmHg).

The visual pass/fail indicator 14 as shown are easily seen through ports 4 (holes or windows) in the body of the apparatus. As the inner tube 8 moves against the pressure of the spring 15, the ratchet engages compressing the spring 5. An audible click is designed as the signal that a pass/fail point has been reached. In a preferred embodiment, a stop mechanism can prevent the ocular plate from traveling further no matter how much pressure is applied. One possible format for the visual indicator(s) is green for pass and red for fail. This may be achieved, for example, by coloring the inner piston 8 green for "pass" and a band 14 of red for "fail". Rather than color coding a readable code, such as a numeric or alpha character may be positioned on the inner piston 8 so that the character is readable when the spring is compressed 5 after the ratchet mechanism 7 is triggered. If several PASS/FAIL thresholds are available, the different thresholds may be coded, for example, numerically or by color.

Figure 1:
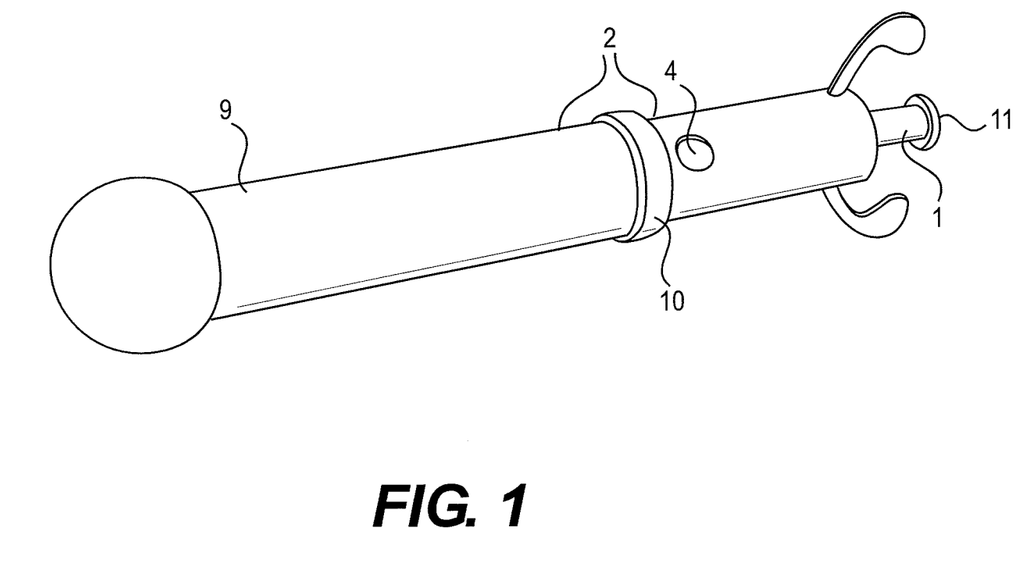
FIG. 1 shows an angle view of the exterior of the apparatus from distal to proximal end.
Figure 2:
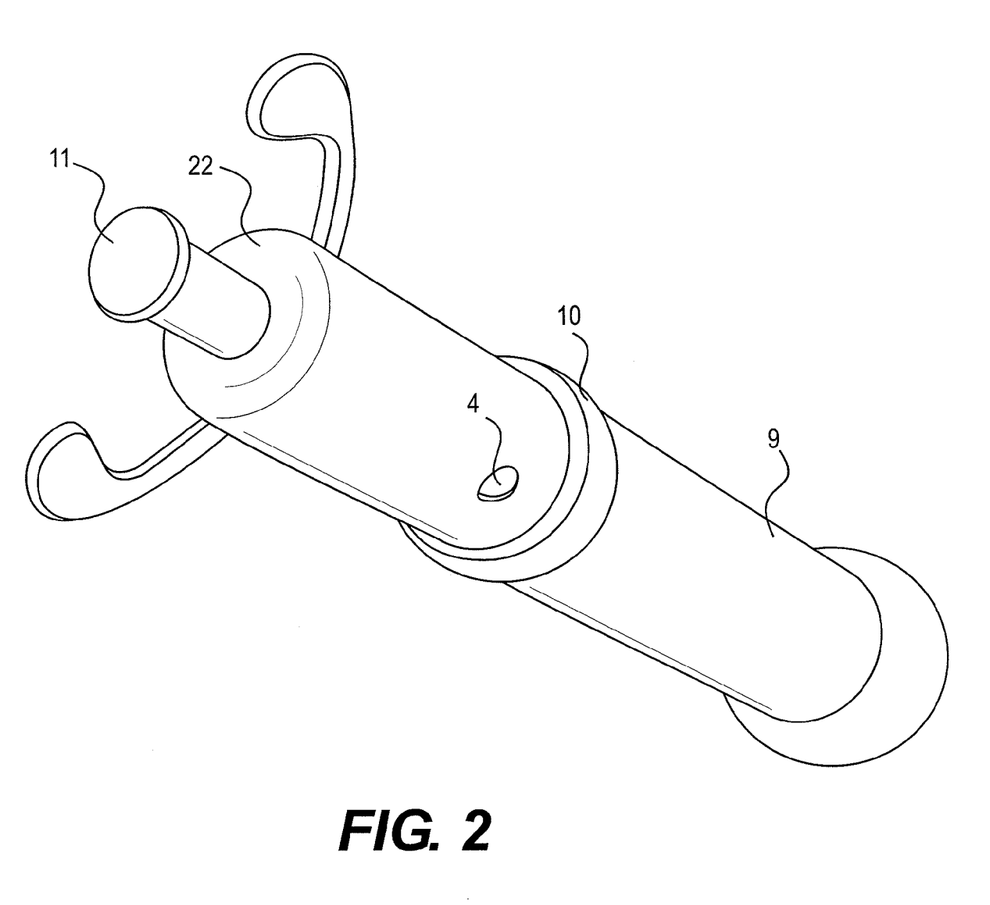
FIG. 2 shows an angle view of the exterior of the apparatus from proximal to distal end.
Figure 3:
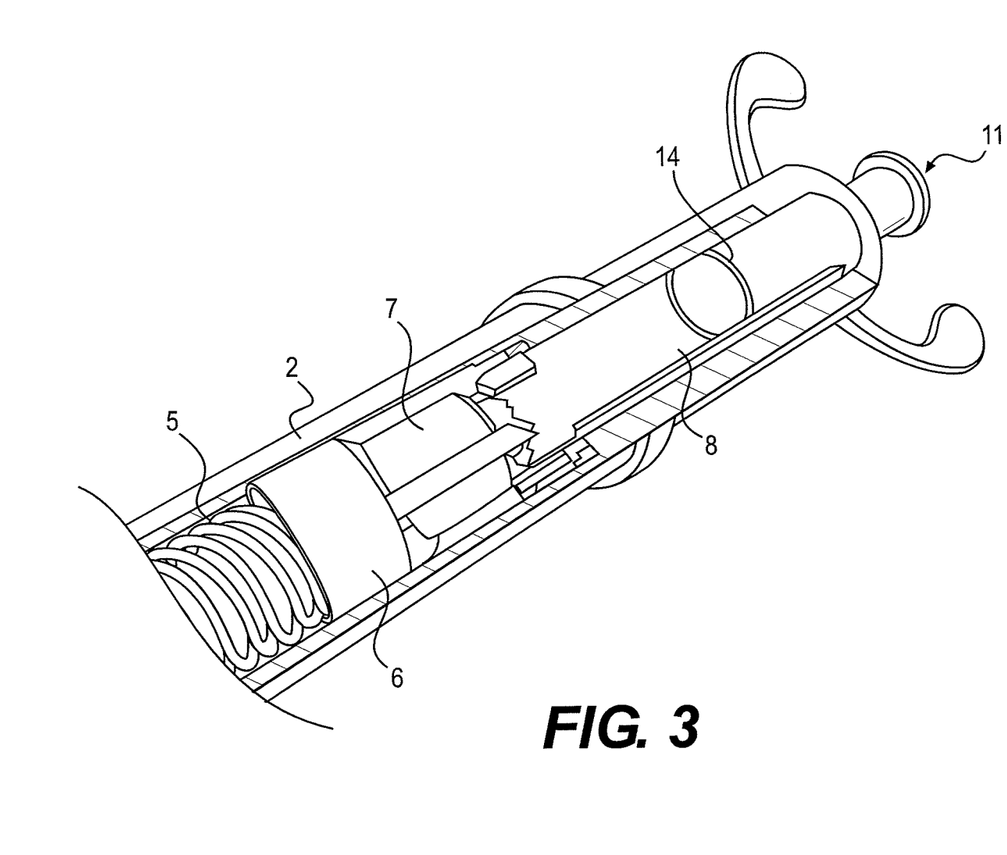
FIG. 3 is a cutaway that shows a view of the apparatus with a compressed spring.
Figure 4:
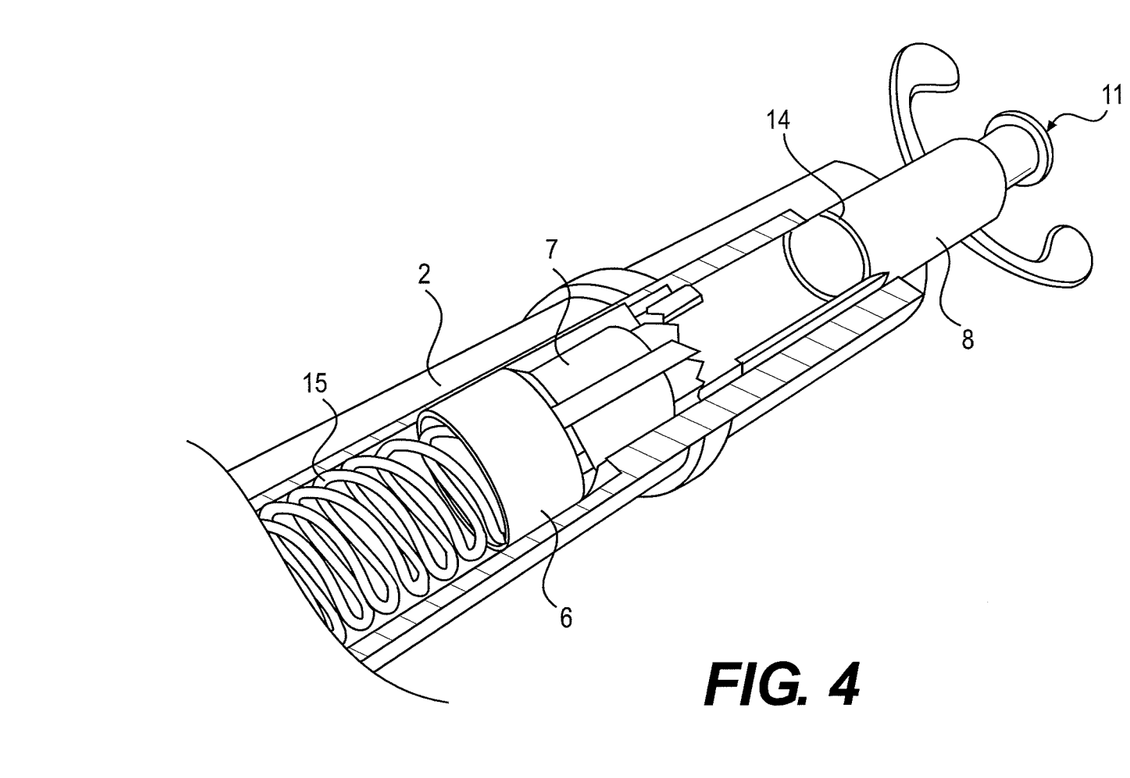
FIG. 4 is a cutaway that shows a view of the apparatus interior in its ready for testing position with a more relaxed spring.
Figure 5:
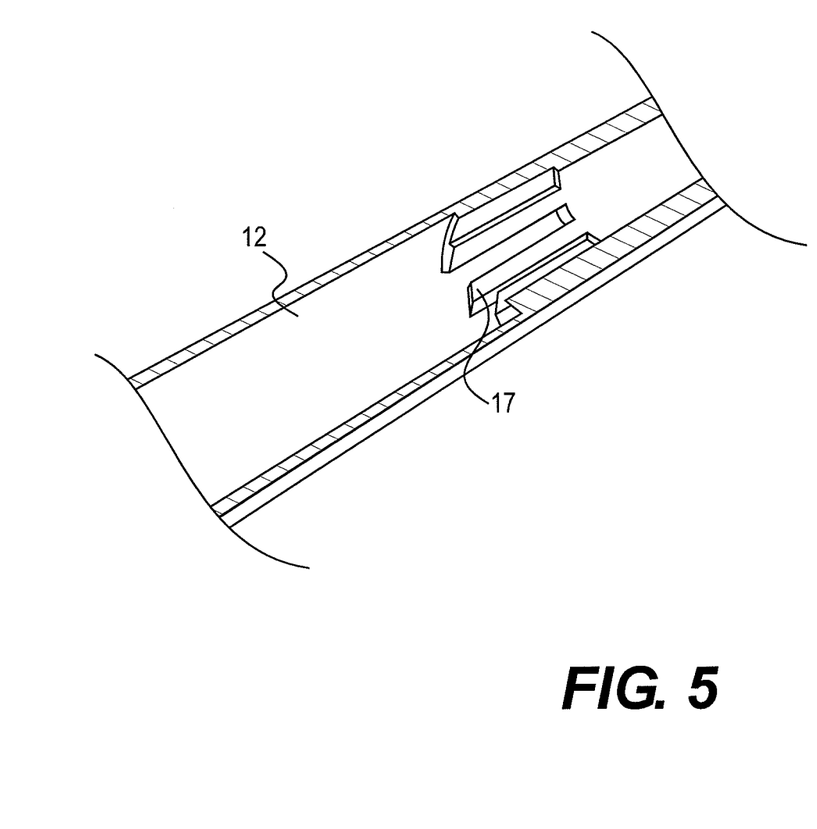
FIG. 5 shows the piston a cutaway view of one possible placement of a portion with the ratcheting mechanism.
Figure 6:
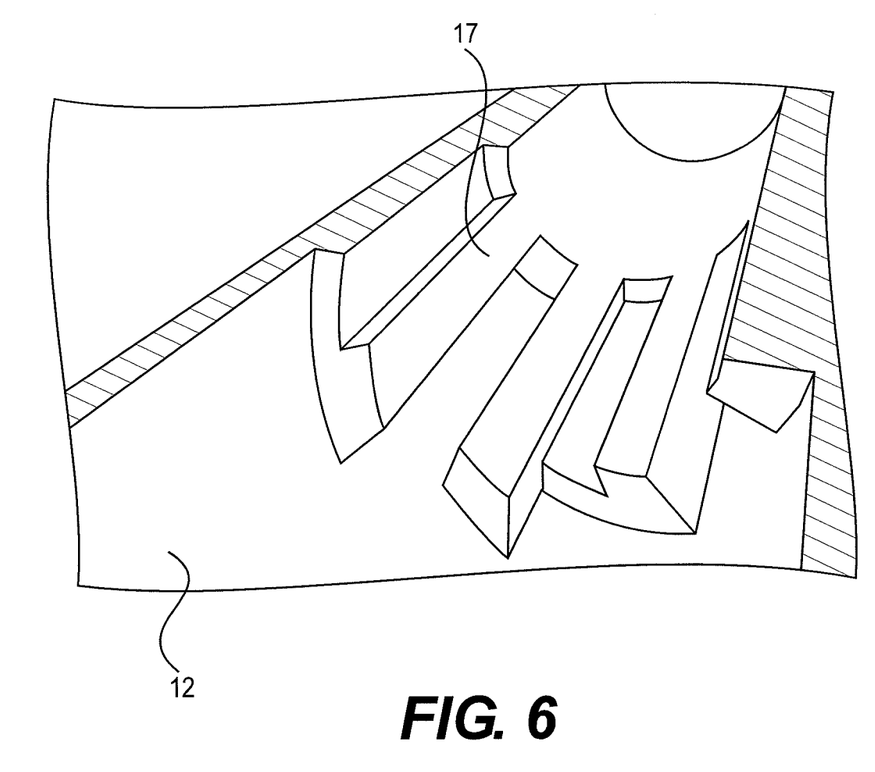
FIG. 6 shows a close up view of the interior ratcheting mechanism.

The apparatus as shown in FIG. 6 has an inner surface 12 of a front end of an outer tube 2 that is arranged with a plurality of axial guiding rails 17. The inner tube 8 is disposed in the outer tube 2 with its front end 1 extending from the front end 22 of the outer tube 2. An ocular plate 11 at the end of the inner tube 1 extends past the opening of the outer tube 2. The ocular plate 11 may sport a symbol on its front end; a symbol or design such as this may be helpful to a user as the user could focus on it, just before the eye closes. The apparatus would then be pressed against the user's closed upper eyelid, avoiding contact with the eyeball itself.

In this example, the anterior half of the apparatus 2 holds the ratchet 7, indicators 14 and a front portion of the spring compartment 6. The posterior or distal half 9 of the apparatus is also strategically sized to accept springs 5 of varying compressions. The distal half 9 of the apparatus may correspond to the dimensions of the spring compartment 6 in the anterior section of the apparatus. For simplicity and ease of obtaining parts, radii of springs, compartments and pistons may correspond to dimensions commonly used in available ratcheting devices, for example, a ball point pen.

The distal half 9 of the apparatus, like the anterior member 22 is fitted so that the two halves can be mated and locked into place. Screw type threads would be an acceptable means for accomplishing the proper mating. Once mated, the anterior 22 and posterior 9 compartments for the spring 5, 15 will not allow the spring 5, 15 to distort or crimp. A ring 10 is shown near the mating portion of the two halves. This is merely meant to signify a grip feature on the exterior of the apparatus. The grip can be configured in any desirable shape which may depend on the design, diameter, length weight, etc. of the apparatus.

EXAMPLES

Example 1

The clinically acceptable model apparatus may be preloaded with springs that correlate to Goldmann IOP readings and/or may be customizable by inserting specific springs into the mechanism.

Springs with compression values that correlate to Goldmann mmHG values at calibrated pressures will cause the cam/ratchet to engage, solicit an audible click, and display a visual indicator when the pressure is exceeded.

For instance, a spring that is manufactured to compress at 10 mmHG will cause the cam/ratchet to engage at 10 mmHg with acceptable tolerances (+/−2 mmHg).

The same is true for springs with full compression equal to 12, 14, 16, 18, 20 and 22 mmHg.

Each apparatus may be coded, for example by color, to indicate the pressure to which the springs are calibrated. The springs themselves may be colored to indicate calibration value. A window (view port) in the housing may allow viewing of the spring to indicate calibration.

Example 2

Only at the "Fail Point" of for example, 22 mmHg or higher, is there a possibility for the subject to continue to exert pressure on the eyelid plate. Therefore the utility for a protective adjunct, such as eyebrow, orbit/cheek restraints may be more desirable for the apparatus with single spring equivalents of 22 mmHg and above. The preloaded or adaptable apparatus will be given to subjects by clinicians, with specific instructions such as, "stop applying pressure against the eyelid when you hear the apparatus "Click." Again, the 10, 12, 14, 16, 18, 20 and 22+mmHg equivalents will cam/ratchet engage at those points within tolerances and before the subject would need to apply additional pressure on the eyelid plate.

Apparatus fitted (either preloaded or adaptable) with 10, 12, 14, 16, 18, 20 and 22+mmHg spring equivalents will cause the cam/ratchet mechanism to engage at these maximum spring compressions. At the point of engagement, the apparatus provides an audible "Click" and a visual indicator.

The apparatus may be manufactured to accept springs inserted, for example, by unscrewing and rescrewing the two halves. This allows the apparatus fail point to be determined by choosing the spring. The apparatus may be manufactured preloaded with a specific spring and possibly coded to indicate calibrated fail point.

The apparatus may be combined with other apparatus in a set, for example, a 10 mmHg, a 14 mmHg, an 18 mmHg and a 22 mmHg calibrated apparatus as a set. Such set could be used starting with the highest desired calibration first. If the pressure was exceeded (click or "fail" signal) a higher calibration apparatus could then be used to check for higher IOP. The process may repeat until the highest calibrated pressure is exceeded.

Example 3

The length, gauge, pitch and diameter of the spring are not critical. The spring and chamber size (interior or the apparatus and the spring compartment) must be sized to accommodate the spring. The inside chamber may be compartmentalized to correspond to the design length and travel of the spring. The outside length can be adjusted to the hand size and grip of the target population for the particular design. These dimensions can be varied to provide for a selected range of stable springs for various pressures and length of compression.

Springs of suitable size and compressibility are commercially available. Similar springs have been used in common ratcheting devices. Precision calibration is possible using one of several materials. Stainless steel is a common spring material. The pitch, length, installed compression and gauge are selected to be calibrated to the desired pass/fail IOP.

Example 4

Since the device can be configured to include an optical indication of pass/fail, an IPhone or other smart apparatus may be used to photograph the visual indicator at scheduled intervals, the image can be processed electronically to easily and reliably document the result, date and time. That data could then be sent electronically to a physician or stored for later analysis.

Additional examples may include: a device having a variable distance follower and shaft change only spring, a device having an inner diameter similar to a pen, with the outer diameter larger for better handling, and a device having an inside hollow similar to a pen, with a cam and follower as stock items.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. An apparatus for indicating intraocular pressure (IOP), comprising:
   i) a probe comprising an ocular plate to contact an eye;
   ii) an inner piston driven by said probe;
   iii) a calibrated spring compressed by movement of said probe, wherein said calibrated spring is selected so as to have a compression force that yields a mechanical, visual pass/fail indication only at a predetermined intraocular pressure value selected from a range from 10 mmHg to 28 mmHg;
   iv) a ratchet mechanism with an endpoint for said probe induced movement;
   v) an indicator that is caused to move by movement of said piston and is caused to rotate and latch by said ratchet mechanism to provide a mechanical, visual indication of a test pass or fail reading at only the predetermined intraocular pressure value from said probe movement, wherein said mechanical, visual indicator is coded to indicate pass or fail, wherein fail indicates that said intraocular pressure value for which said spring is calibrated has been surpassed; and
   vi) a housing for aligning said inner piston, spring, ratchet, indicator and probe.

2. The apparatus of claim 1 wherein the indicator is viewable through a port in said housing.

3. The apparatus of claim 1, wherein said housing comprises a plurality of sections, said sections capable of disassembly permitting substituting said spring with a replacement spring.

4. The apparatus of claim 1, further comprising a shield coordinated with said housing, said shield aiding positioning of said apparatus by contact of said shield adapted to make contact with a bony orbit surrounding an eye, said shield coordinating with said probe to prevent further inward pressure with an eyelid covering said eye.

5. A kit comprising the apparatus of claim 1, said kit further comprising a second spring, said second spring having a compression force 2 that differs from a compression force 1 of said calibrated spring, so as to provide a mechanical, visual pass/fail indication at a different predetermined intraocular pressure value.

6. A composite set comprising a plurality of apparatus of claim 1, wherein a plurality of indicators are coordinately paired with corresponding calibrated springs, said indicators coded to indicate pass or fail corresponding to the IOP value for which said spring is calibrated.

7. The apparatus of claim 1 wherein the predetermined intraocular pressure value is selected from a range between 10 mmHg and 22 mmHg.

8. The apparatus of claim 1 wherein the predetermined intraocular pressure value is set in a range +/−2 from a value selected from the group consisting of 10 mmHg, 14 mmHg, 18 mmHg and 22 mmHg.

9. The apparatus of claim 1 wherein the predetermined intraocular pressure value is selected from a range between 16 mmHg and 28 mmHg.

10. A method for monitoring intraocular pressure comprising:
    providing an apparatus including a probe, an inner piston driven by said probe, a calibrated spring compressed by movement of said probe, wherein said calibrated spring is selected so as to have a compression force that provides a mechanical, visual pass/fail indication only at a predetermined intraocular pressure value selected from a range from 10 mmHg to 28 mmHg, a ratchet mechanism with an endpoint for said spring induced movement, an indicator that is caused to move by movement of said piston and is caused to rotate and latch by said ratchet mechanism to provide a mechanical, visual test pass or fail reading at only the predetermined intraocular pressure value from said probe movement, wherein said mechanical, visual indicator is coded to indicate pass or fail, wherein fail indicates that said intraocular pressure value for which said spring is calibrated has been surpassed, and a housing for aligning said inner piston, spring, ratchet, indicator and probe; and
    applying a force to an eyelid with said probe until said apparatus indicates a test pass or fail reading.

11. The method of claim 10, wherein said eyelid is a human eyelid.

12. The method of claim 10, wherein said eyelid is a dog eyelid.

13. The method of claim 10, wherein said eyelid is a horse eyelid.

14. The method of claim 10, wherein the predetermined intraocular pressure value is selected from a range between 16 mmHg and 28 mmHg.

* * * * *